United States Patent [19]

Oloff et al.

[11] Patent Number: 4,913,143
[45] Date of Patent: Apr. 3, 1990

[54] TREPHINE ASSEMBLY

[75] Inventors: Clarence M. Oloff; Harry T. Moore, both of Dayton, Ohio

[73] Assignee: The United States of America as represented by the Secretary of the Air Force, Washington, D.C.

[21] Appl. No.: 867,728

[22] Filed: May 28, 1986

[51] Int. Cl.⁴ .............................................. A61F 17/32
[52] U.S. Cl. ..................................... 606/170; 606/179
[58] Field of Search ............................. 128/305.1, 310; 408/703, 203

[56] References Cited

U.S. PATENT DOCUMENTS

| | | | |
|---|---|---|---|
| 2,919,692 | 1/1960 | Ackermann | 128/2 |
| 3,605,721 | 9/1971 | Hallac | 128/2 B |
| 3,628,524 | 12/1971 | Jamshidi | 128/2 B |
| 3,893,445 | 7/1975 | Hofsess | 128/2 B |
| 3,913,566 | 10/1975 | Lacey | 128/310 |
| 4,099,518 | 7/1978 | Baylis et al. | 128/310 |
| 4,122,855 | 10/1978 | Tezel | 128/310 |
| 4,142,517 | 3/1979 | Stavropoulos et al. | 128/310 |
| 4,262,676 | 4/1981 | Jamshidi | 128/310 |
| 4,306,570 | 12/1981 | Matthews | 128/754 |
| 4,341,206 | 7/1982 | Perrett et al. | 128/310 |
| 4,600,014 | 7/1986 | Beraha | 128/310 |

FOREIGN PATENT DOCUMENTS

| | | | |
|---|---|---|---|
| 48401 | 1/1984 | German Democratic Rep. | 408/203 |

*Primary Examiner*—C. Fred Rosenbaum
*Assistant Examiner*—Sharon Rose
*Attorney, Agent, or Firm*—Gerald B. Hollins; Donald J. Singer

[57] ABSTRACT

A hollow trephine cutter unit capable of disassembly to provide damage-free access to the collected sample or to permit size changes of the cutting element. Disassembly by sliding movement of one element of the apparatus with respect to the other and multiple torque transmission paths between prime mover and cutting element are also disclosed. Multiple function use of the prime mover chuck and easy cutter unit disassembly despite the presence of organic fouling are also provided.

15 Claims, 2 Drawing Sheets

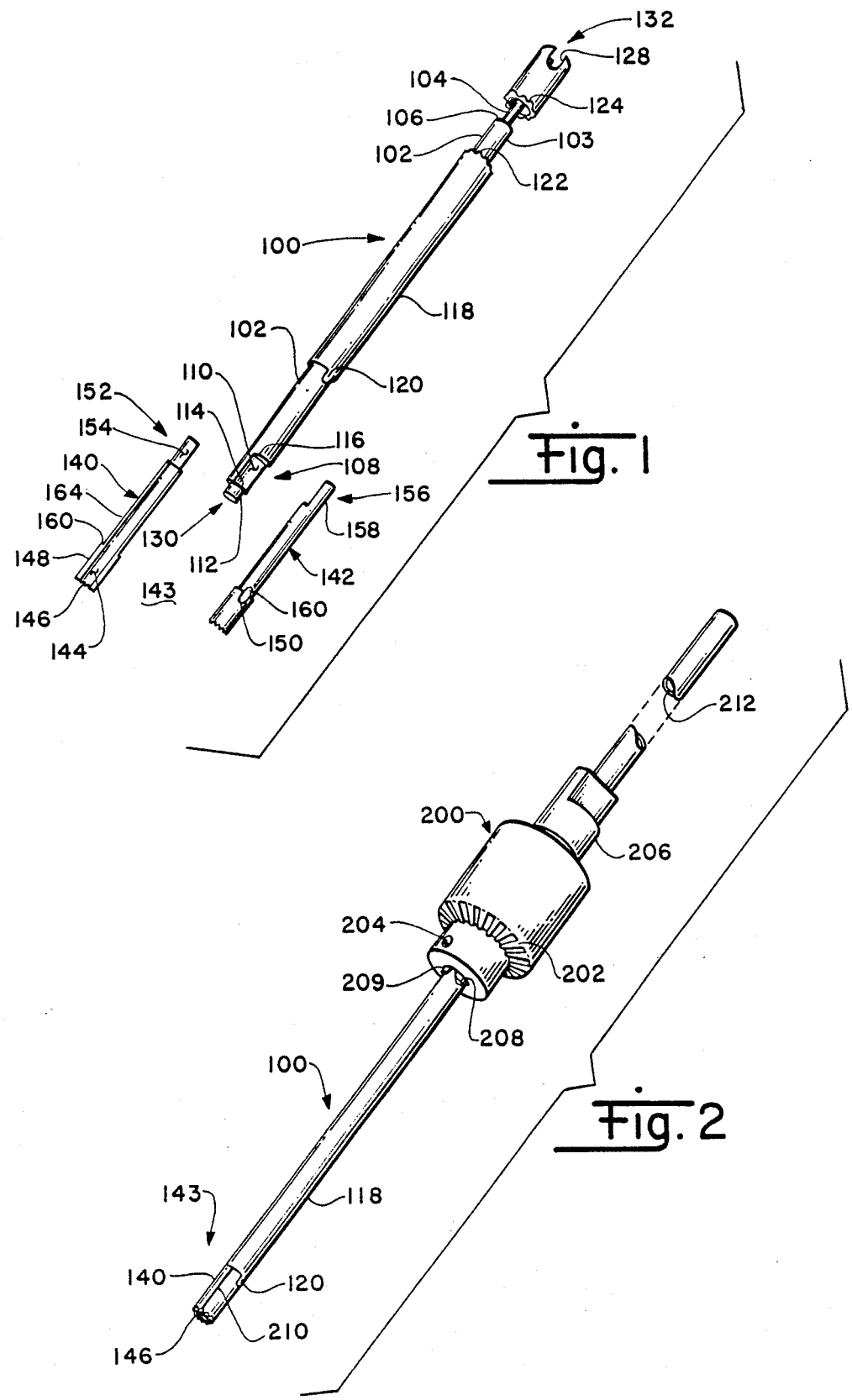

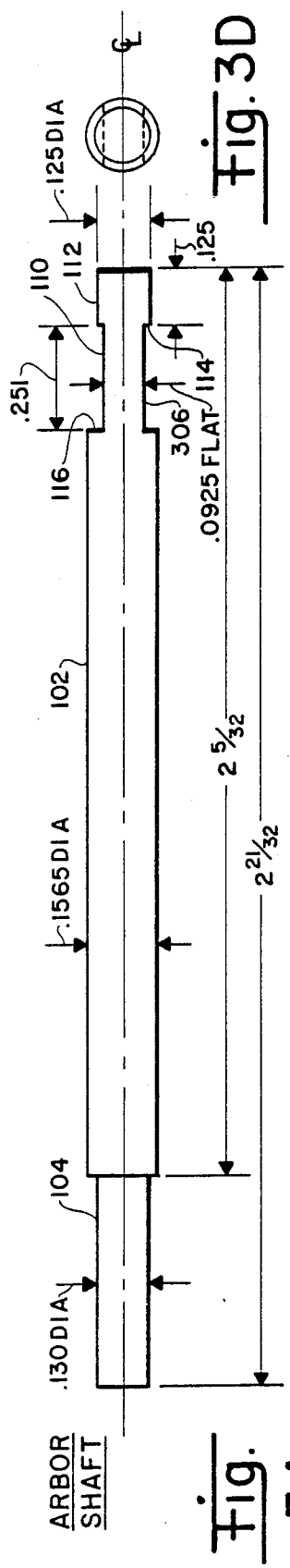
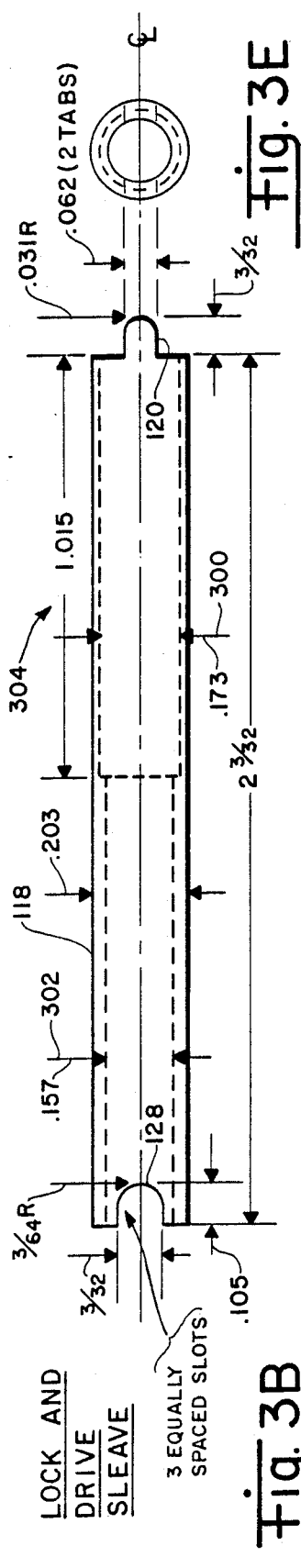
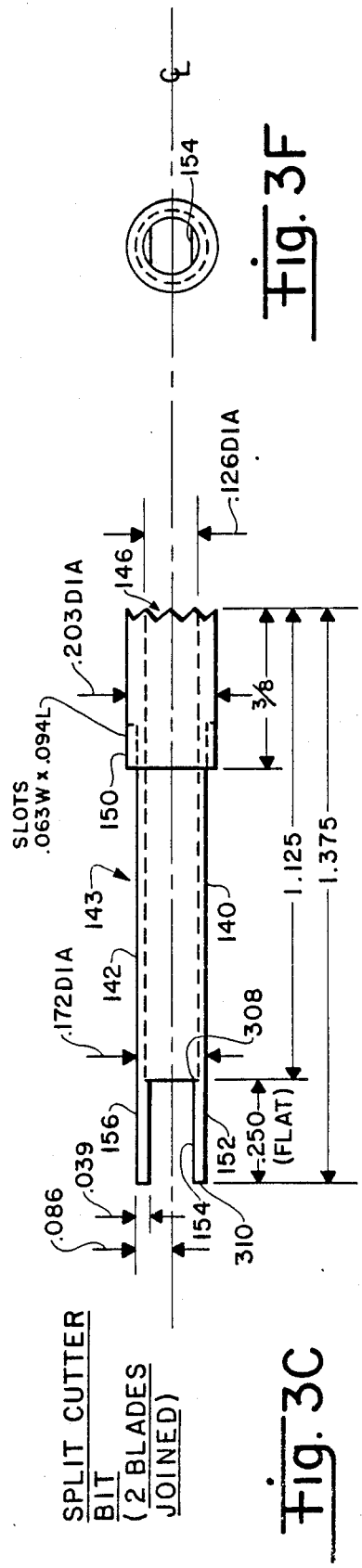

TREPHINE ASSEMBLY

RIGHTS OF THE GOVERNMENT

The invention described herein may be manufactured and used by or for the Government of the United States for all governmental purposes without the payment of any royalty.

BACKGROUND OF THE INVENTION

This invention relates to the field of trephine cutting tools of the type used for obtaining samples from humans, animals, and other living or deceased specimens.

In the treatment and study of disease and the therapeutic processes and in biomedical studies such as space medicine bone study, it is desirable to collect small specimens of bone from a vertebrate test subject for microscopic and other laboratory study. A guiding and supporting arrangement for conveniently and safely collecting such samples is, for example, shown in the copending patent application, having one common inventor herewith, Ser. No. 06/751,393, filed Jul. 3, 1985 and issued 31 Mar. 1987 as U.S. Pat. No. 4,653,509, and deals principally with accurately positioned sample collection from small animal test subjects.

The use of a hollow annular cross-sectioned drill bit having small sawteeth disposed at the working end thereof, i.e., a trephine cutter, for the collection of tissue samples from living test subjects has been known for some time. A frequent problem with the known sample collecting arrangements occurs, however, during the post-sample collection steps wherein the sample is removed from the trephine cutter bit. Heretofore it has been common practice to employ hydraulic pressure or a push rod or some similar forcing apparatus for disengaging the collected sample from the trephine cutter bit. In the course of this disengagement, sufficient pressure is often applied to the collected sample to cause compression damage or sample density alteration as a by-product of the disengagement sequence. For most present-day study purposes, such disturbances of the collected sample are a disabling, sample-destroying consequence. An awareness of such destructive effects occurring during sample collection is, for example, indicated in the article "Closed Vertebral Biopsy" by L. S. Fyfe, A. P. J. Henry, and R. C. Julkolland, published in the Journal of Bone and Joint Surgery, Vol 65-B, No. 2, Mar. 1983, wherein the collection of tissue specimens of two millimeters diameter or more is suggested for best accuracy. In the case of bone samples, the tendency of sampled tissue to clog or obstruct the sample collecting apparatus has in particular been a problem with the existing trephine arrangements. The periosteum tissue surrounding bone members in a vertebrate specimen has particular affinity for surgical instruments and thereby materially complicates the sample retrieval process using most existing trephine equipment.

The patent art discloses inventive attention to the field of trephine sample collection. This attention is evidenced in the patents of W. Ackerman, U.S. Pat. No. 2,919,692; I. Hallac, U.S. Pat. No. 3,605,721; K. Jamshidi, U.S. Pat. No. 3,628,524; P. W. Hoffsess, U.S. Pat. No. 3,893,445; and L. S. Matthews, U.S. Pat. No. 4,306,570, all of which concern trephine or biopsy sample apparatus providing some arrangement for disengaging the collected sample—arrangements such as a push rod extruder or multiple collecting device diameters. It may be noted, however, that none of these patents is concerned with a trephine sample collecting arrangement wherein the cutter bit can be disassembled to provide convenient access to the sample and also assure the absence of compression disturbances to the sample. The prior art has therefore been unable to provide a fully satisfactory apparatus for collecting high-quality trephine samples conveniently and practically.

SUMMARY OF THE INVENTION

An object of the present invention is to provide a trephine sample collecting apparatus wherein access to the collected sample can be achieved with a minimum of disturbance to the sample.

Another object of the invention is to provide a split trephine sample collecting apparatus.

Another object of the invention is to provide a trephine sample collecting apparatus wherein disassembly of the collecting apparatus is readily achieved, despite the presence of interfering tissue and fluids.

Another object of the invention is to provide a trephine sample collecting apparatus which provides a plurality of torque transmitting paths between the prime mover apparatus and the trephine cutter bit.

Another object of the invention is to provide a trephine sample collecting apparatus which is responsive to driving torques in either rotational direction.

Another object of the invention is to provide a trephine apparatus wherein a plurality of differently sized sample collecting bits can be used with a single cutter bit mounting and driving apparatus.

Another object of the invention is to provide a trephine apparatus which can be powered by a variety of different prime mover devices such as a pneumatic drill, an electric drill, or a manually-powered drill.

Another object of the invention is to provide a trephine apparatus wherein the clamping action of a prime mover drill chuck serves a plurality of utility functions with respect to the trephine apparatus.

Additional objects and features of the invention will be understood from the following description and the accompanying drawings.

These and other objects are achieved by a trephine sample collecting apparatus including a circular arbor shaft member, a cylindrical sleeve member telescopically received over the arbor shaft member, a circumferentially segmented cutter bit engageable in torque transmitting relationship with an end portion of one of the arbor shaft and sleeve members, and in axial position fixed relationship with one of the arbor shaft and sleeve members and retained in the relationship in response to predetermined relative telescopic positioning of the arbor shaft and sleeve members, driving chuck means for both rotationally engaging one of the arbor shaft and cylindrical sleeve members at the cutter bit opposite end thereof and for simultaneously clamping the members in predetermined relative telescopic position.

BRIEF DESCRIPTION OF THE DRAWINGS

FIG. 1 is an exploded perspective view of a trephine assembly made in accordance with the invention.

FIG. 2 is an assembled view of the FIG. 1 apparatus and an associated prime mover driving chuck.

FIG. 3 (A–F) shows additional structural details and dimensions for one embodiment of the invention.

DETAILED DESCRIPTION

FIG. 1 in the drawings depicts an exploded, perspective, cutaway, view of a trephine cutter assembly made in accordance with the invention. In FIG. 1, the trephine cutter unit 100 is shown to include an arbor shaft member 102 which is received telescopically within a cylindrical sleeve member 118, along with a pair of cutter bit segments 140 and 142. The cutter bit segments 140 and 142 are receivable on the arbor shaft 102 and together comprise a circumferentially segmented cutter bit 143 when placed in the cutter assembly relationship shown in FIG. 2 of the drawings.

The cylindrical sleeve member 118 in FIG. 1 is shown in an axially withdrawn or telescoped position that is short of the fully assembled position represented in FIG. 2 of the drawings. The sleeve 118 is also shown broken or cut away, in FIG. 1, as is indicated by the break lines 122 and 124 in order that an upper portion of the arbor shaft 102 including the annular ridge 106 is visible. The reduced diameter upper shank 104 joins the body portion of the arbor shaft 103 at the annular ridge 106, as is visible between the sleeve cutting lines 122 and 124.

The sleeve 118 which may be called a lock and drive sleeve, includes a pair of tabs or tangs located at the cutter bit end thereof; one of these tabs or tangs is shown at 120 in FIGS. 1 and 2 of the drawings. The tabs or tangs 120 serve as a torque transmitting disengageable connection between the sleeve 118 and the cutter bit segments 140 and 142 as is more fully explained below. The cutter bit opposite or driven end of the sleeve 118 is indicated at 132 in FIG. 1. This sleeve end includes a plurality, preferably three, axially extending slots 128 which serve to engage the jaws of a Jacobs ®-type drill chuck, while these jaws are frictionally seated on the arbor shaft 102 in a torque transmitting relationship as is shown in FIG. 2 of the drawings.

The cutter bit end of the arbor shaft 102 is indicated at 130 in FIG. 1, and includes a pair of machined flat areas or regions of varying radius 110 located in a shaft axial region 108. The flat 110 is therefore one of a pair of flats existing on the arbor shaft 102 as is better discernible in FIG. 3A of the drawings. Also located at the cutter bit end of the arbor shaft is a short cylindrical section 112 which is preferably of smaller diameter than the body 103 of the arbor shaft 102, but of larger diameter than the space between opposed flats 110 in order that the circumferential ridge 114 which serves a blade segment retention function as described below, is achieved. The circumferential ridge wherein the flat 110 joins the body of the arbor shaft 102 is indicated at 116 in FIG. 1.

The cutter bit 143, comprised of the segments 140 and 142 is also shown to include a plurality of annularly disposed cutting teeth 146 located at the outward end of a large diameter cutter bit portion 148. The teeth 146 are preferably symmetrical with respect to the shaft axis and therefore are bi-directional in their cutting ability. The shank portion 164 of the cutter bit is of reduced diameter with respect to the portion 148 and is as indicated in FIG. 2, receivable within the internal diameter of the sleeve 118 at the cutter bit end thereof—when the sleeve 118 is in the operating position shown in FIG. 2 of the drawings.

The cutter bit segments 140 and 142 each have a circular internal surface portion 144 which receives the removed sample. Each cutter bit segment also includes an ear portion indicated at 152 and 156 in FIG. 1. The ear portions 152 and 156 each also incorporates internal flat surface area as is indicated at 154 for the cutter bit segment 140. The flat surface area portion 154 is received on one of the flats 110 and 306 in the assembled condition of the trephine cutter unit shown in FIG. 2 and serves in this position as a torque transmitting connection with the arbor shaft 102. The exterior surface of the ears 152 and 156 is rounded in nature and is of course, received in close fitting conformity with the interior diameter of the sleeve 118 in the position of the elements shown in FIG. 2. The cross-sectional area of each of the ear portions 152 and 156 is therefore of the shape of a capital letter "D" or a chord terminated segment of a circle.

Located on each of the exterior surfaces of the cutter blade segments 140 and 142 is a slotted or indented region 150 in which is received the tab or tang members 120 of the sleeve 118 which accomplishes torque transmission between the sleeve and the cutter bit 143. Although the slotted or indented region 150 may reside in both the large diameter portion 148 and the smaller diametered shank portion 142, of the cutter bit depending upon the accuracy of the machining depth cut, the large diameter portion is the primary torque transmitting structure as is discernible in FIG. 2 of the drawings.

The circumferential shoulder 160 at the interface of the cutter bit large diameter portion 148 and shank portion 164 appears as merely a line in the assembled version of the cutter bit unit shown in FIG. 2—when the cutter bit 143 is made to have the same diameter as the sleeve member 118. The shoulder 160 will of course, be more visible in other embodiments of the invention where the large diameter portion of the bit 148 is of greater diameter than the sleeve 118. In such arrangements, the large diameter portion may be desirably tapered and/or the circumferential shoulder 160 rounded to minimize the tendency of the shoulder 160 to become caught in tissue, especially during removal of the trephine cutter unit from a test subject.

FIG. 2 of the drawings shows the assembled, ready-to-use condition of the trephine cutter unit 100 as it is received in a chuck of the Jacobs ® type—a chuck which may be part of, for example, an air turbine powered drilling unit. Parenthetically, it should be explained that in the FIG. 2 view of the trephine cutter unit 100, the elements identified and discussed in FIG. 1 are provided with the FIG. 1 indicating number, while elements that are newly described in FIG. 2 are given numbers in the 200 series. According to this arrangement therefore, the junction of the cutter bit segments 140 and 142, is shown at 210 in FIG. 2, and elements connected with the chuck 200 are indicated by additional numbers in the 200 series. The number 202, for example, indicates the tightening teeth of the chuck. Such teeth may be actuated by a geared chuck key inserted in the hole 204. The number 206 indicates the chuck shaft. Similarly, a movable jaw of the chuck 200 is indicated at 208 in FIG. 2, and the hollow interior of the shaft 206 is indicated at 212.

In the assembled condition of the trephine cutter unit shown in FIG. 2, the chuck jaws 208, 209, and a third jaw which is not shown in FIG. 2 grasp the cylindrical surface of the arbor shaft 102 in an axial region immediately below its reduced diameter upper shank portion 104 and thereby provide a means for transmitting torque between the chuck 200 and the arbor shaft 102.

The transmitted torque is, of course, thence delivered to the cutter bit 143.

As indicated in FIG. 2, during this grasping of the arbor shaft 102 by the chuck jaws 208 and 209, the chuck jaws reside in the axially extending slots 128 of the sleeve member 118, that is, the chuck jaws pass through the slots 128 in reaching the cylindrical surface of the arbor shaft 102. By this arrangement, the chuck jaws provide rotational torque to both the arbor shaft 102 and to the cylindrical sleeve 118 and a parallel path torque transmission to the cutter bit 143 is established. In this parallel path arrangement, one of the paths is of course, through the cylindrical sleeve 118 and the other path by way of the arbor shaft 102. Both of these paths achieve a torquewise connection with the cutter bit 143—by way of the torque transmitting flats arrangement at 110 and 154 for the arbor shaft 102 and by way of the tabs 120 and slotted regions 150 for the sleeve 118.

It is interesting to note that as an incident of this parallel path torque transmitting arrangement the chuck 200 actually serves four separate functions or purposes in the described embodiment of the invention. These functions include: (1) torque transmission to the arbor shaft 102, (2) torque transmission to the cylindrical sleeve 118, (3) retention of the sleeve 118 in the predetermined axial position with respect to the arbor shaft 102 (wherein engagement of the tabs 120 with the slotted region 150 is maintained) and (4) protection of the upper or driven portion of the arbor shaft 102 from tissue contamination, splattering, or other soiling during use of the trephine assembly.

The latter function is of notable practical significance when disassembly of the sample-containing trephine cutter unit is to be accomplished after a sample collection procedure. By way of this protection of the arbor shaft 102 by the chuck 200, the sleeve 118 is assured of a clean and unobstructed axial sliding travel over the upper or driven portion of the arbor shaft 102 during knockdown of the assembly and release of the cutter segments 140 and 142.

The reduced diameter upper shank 104 of the shaft 102 in FIG. 1 is intended for reception in the hollow interior 212 of the chuck shaft 206. In some arrangements of the invention, of course, depending upon the size of the arbor shaft 102 and the size of the chuck shaft hollow interior, such reduced diameter for the upper arbor shaft portion may not be required—the arbor shaft may be received within the chuck shaft 212 without interference. The reduced diameter portion 104 may be desirable, however, with the use of small chucks or if the FIG. 1 and FIG. 2 apparatus is used with a chuck or gripping device of some alternate type.

Additional details of the FIG. 1 and FIG. 2 trephine cutter unit are shown in FIG. 3 of the drawings. FIG. 3 includes the lateral views [FIGS.] 3A, 3B and 3C, and the end views [FIGS.] 3D, 3E and 3F. The FIG. 3 views show dimensions for a trephine cutter unit of 0.203 inch outer diameter and 0.126 inch inner diameter—the 0.126 inch inner diameter is, of course, the diameter of the collected sample.

In addition to the dimensions shown in FIG. 3, certain other details of the FIG. 1 and FIG. 2 embodiment of the invention that are not readily viewable in FIG. 1 and FIG. 2 are also shown in FIG. 3. These details include the second region of varying radius or flat 306, shown in FIG. 3A, and the enlarged internal diameter 300 at the cutter end of the sleeve 118. The enlarged diameter sleeve region serves to receive the ears 152 and 156 and the shank portion 164 of the cutter bit 143 in the engaged and assembled conditions of the FIG. 1 and FIG. 2 apparatus. In alternate embodiments of the invention, use of the enlarged internal diameter 300 may not be necessary, depending upon the relative sizes of the parts and the required torque transmitting capability in the ears 152 and 156. In such arrangement the diameters 302 and 300 may be of the same dimension. The length 304 of the enlarged diameter region is of course, adjusted according to the length of the cutter bit shank portion, 164 in FIG. 1, and in response to the desired length of the collected test subject sample.

Another detail of the FIG. 1 and FIG. 2 trephine cutter unit that is most clearly shown in FIG. 3 is the circular to flat shoulder 308. The shoulder 308 serves to retain the cutter bit 143 captured on the arbor shaft 102 during pullout or retrieval of the trephine cutting unit 100 and the collected sample residing therein from the test subject. The circular to flat shoulder 308 therefore engages the circumferential ridge 114 on the arbor shaft 102 in the assembled condition of the FIG. 1 and FIG. 2 apparatus-in order to provide axial unity to the trephine cutter unit. In a similar manner, the upper extremity shoulder 310 of the cutter bit 143 engages the circumferential ridge 116 of the arbor shaft 102 to positively locate the cutter bit 143 with respect to the arbor shaft during compression axial loading of the assembly as occurs during insertion or cutting actions with the trephine cutter unit. The teeth 146 which are disposed annularly around the end of the cutter bit 143 and are also shown in all three of the drawing figures, are preferably arranged to be bi-directional in nature, that is, to have the profile of an isosceles triangle as opposed to the profile of a scalene or obtuse triangle as would impart a rotational cutting preference. The end views of the FIG. 3A, 3B and 3C apparatus shown in FIGS. 3D, 3E and 3F of FIG. 3, show additional internal and external details of the elements previously described above.

In addition to the differing diameters for the enlarged portion 148 of the cutter bit 143, other variations of the invention are possible. Such variations might include for example, the use of more than two segments in the cutter bit 143, that is, circumferentially dividing the cutter bit into three, four or some other number of segments, and making a corresponding adjustment in the number of flats 110 employed—a square, pentagon, or hexagon shape for the region 108 of the arbor shaft 102 being feasible especially in the case of a larger-diametered trephine assembly. Preferably in such an arrangement each of the cutter segments, such as the segments 140 and 142, is arranged to have a tab and tab receptacle of the type indicated at 120 and 150 in FIGS. 1 and 2. In a similar manner, the sleeve 118 could easily be arranged to accept two or four or some other number of chuck jaws in lieu of the three described above and commonly employed in the tool art.

Yet another variation of the invention could be achieved by disposing the connection between arbor shaft 102 and cutter blade segments at region 108 according to an arrangement other than the recited flats. For example, radially disposed slots with corresponding radial projections from the cutter bit internal surface or a splined cross-sectional shape of cutter bit and arbor shaft or other known torque transmission arrangements could readily be employed. The terms "torque transmitting" and "radius varied areas" are used herein to generically indicate a broad range of possible torque transmitting couplings between the arbor shaft 102 and the cutter bit 143.

The trephine cutter unit of FIGS. 1-3 can be fabricated with many possible materials. Surgical stainless steel or titanium or similar metals which are both machinable and of known resistance to biological fluid attack and corrosion and which present readily cleaned surfaces are the preferred fabrication materials.

IN THE DRAWINGS

Please substitute the enclosed new sheet 2 of drawings including FIGS. 3A, through 3F for the originally filed sheet 2 of drawings. The new sheet 2 of drawings differ from the originally filed sheet in spelling the word "sleeve" in FIG. 3B. The trephine cutter unit is of course, well adapted to the retrieval of hard tissue, i.e., bone samples, but may in addition be deployed in muscular, tendon, or other firm tissues to obtain samples.

The retrieved sample once withdrawn from the test subject, is accessible in the FIG. 1-3 apparatus upon axial movement of the sleeve 118 from the position of engagement with the cutter bit 143 as shown in FIG. 2 in the drawings. It can be appreciated that such movement is greatly facilitated by the clean upper surface of the arbor shaft 102 and by the simple axial telescopic sliding motion required of the sleeve 118 with respect to the arbor shaft 102. Upon sliding withdrawal of the sleeve 118, the FIG. 1 cutter bit segments 140 and 142 of course, separate at the junction 210 to enable easy separation of the collected sample and the cutter bit segments or direct use of the sample while it is yet retained in one cutter bit segment.

The described apparatus therefore provides for the attainment of high-quality accurately positioned trephine samples while also affording a maximum degree of convenience for the operator and a minimum of damage to surrounding tissue in the test subject.

While the apparatus and method herein described constitute a preferred embodiment of the invention, it is to be understood that the invention is not limited to this precise form of apparatus or method, and that changes may be made therein without departing from the scope of the invention, which is defined in the appended claims.

We claim:
1. Trephine sample collecting apparatus comprising:
   a arbor shaft member;
   a hollow sleeve member telescopically received over said arbor shaft member;
   a circumferentially segmented cutter bit engageable in torque transmitting relationship with an end portion of one of said arbor shaft and sleeve member and in axial position fixing relationship with one of said arbor shaft and sleeve member and retained in said relationships in response to predetermined relative positioning of said arbor shaft and sleeve member; and
   driving chuck means for rotationally engaging one of said arbor shaft and sleeve member at the cutter bit opposite end thereof and for simultaneously clamping said members in said predetermined relative position.

2. The apparatus of claim 1 wherein said arbor shaft member is of greater length than said sleeve member and includes an exposed axially extreme non-telescope covered portion received in frictional engagement within multiple chuck jaws of said driving chuck means.

3. Trephine sample collecting apparatus comprising:
   an arbor shaft member;
   a hollow sleeve member shorter than said arbor shaft member and telescopically received over a central portion of said arbor shaft member;
   a circumferentially segmented cutter bit engageable in torque transmitting relationship with an end portion of one of said arbor shaft and sleeve member and in axial position fixed relationship with one of said arbor shaft and sleeve member and retained in said relationships in response to predetermined relative positioning of said arbor shaft and sleeve member;
   multiple jawed driving chuck means for rotationally engaging one of said arbor shaft and sleeve member at the cutter bit opposite ends thereof and for simultaneously clamping said members in said predetermined relative position, said rotational engagement including frictional engagement between said driving chuck means chuck jaws and a cutter bit opposite end portion of said arbor shaft member; and
   said sleeve member including also a plurality of axially extending slots at said cutter bit opposite end thereof with said slots being disposed in surrounding engagement with side portions of said driving chuck means chuck jaws simultaneously with said chuck jaw to arbor shaft frictional engagement.

4. The apparatus of claim 3 wherein said cutter bit includes torque transmitting engagement with end portions of both said arbor shaft and said sleeve members.

5. The apparatus of claim 4 wherein said arbor shaft is circular in cross section and includes an axial region of radius varied areas each matable in torque transmitting relationship with a complementary shaped area of one cutter bit circumferential segment.

6. The apparatus of claim 5 wherein said cutter bit circumferential segments are maintained in closed circumference relationship, and said radius varied and complementary shaped areas are maintained in torque transmitting mating relationship during said predetermined relative telescopic positioning of said arbor shaft and sleeve members and are released from said relationships by axial sliding of said cylindrical sleeve member along said circular arbor shaft in the direction of said exposed non-telescope covered arbor shaft portion.

7. The apparatus of claim 6 wherein each said radius varied area is comprised of a flattened surface having a chord-like relationship with said arbor shaft circular shape and each said cutter bit segment includes a mating axial region of flattened surface interior shape and circular segment exterior shape receivable in torque transmitting relationship intermediate one of said arbor shaft flattened surfaces and the interior surface of said sleeve member.

8. The apparatus of claim 7 wherein said cutter bit is retained in axial position fixed relationship on said arbor shaft member by said predetermined telescopic positioning of said shaft and sleeve members and released therefrom by said axial sliding, said cutter bit segments each including a planar surface to rounded surface shoulder transition located at the cutting surface end of said cutter bit segment flattened surface and engageable for said cutter bit retention with a planar surface to rounded surface shoulder located on said arbor shaft at the extreme cutter bit end thereof.

9. The apparatus of claim 8 wherein said cutter bit segments each include a socket receptacle disposed in the outer periphery thereof and said sleeve member includes a plurality of axially extending tangs each engageable with one of said cutter bit segment socket receptacles in torque transmitting relationship therewith during said predetermined relative telescopic positioning and releasable therefrom during said axial sliding.

10. The apparatus of claim 8 wherein said sleeve member has a first larger internal diameter portion at the cutter bit end thereof, and a second smaller internal diameter portion at said cutter bit opposite end thereof; the internal and external diameters of said cutter bit segments being greater than the diameter of said arbor shaft and being less than said sleeve first larger internal diameter portion respectively.

11. The apparatus of claim 9 wherein said cutter bit comprises two of said circumferential segments and said driving chuck means comprises three of said chuck jaws.

12. The apparatus of claim 10 wherein an axially extreme portion of said exposed non-telescope covered arbor shaft is of reduced diameter and is thereby receivable within a hollow driving shaft portion of said driving chuck means.

13. Trephine cutter apparatus comprising:

an elongated cylindrical sleeve member having a hollow interior portion, a first plurality of axially extending slots located at a first end thereof and a second plurality of axially extending tabs located at the opposite second end thereof;

an elongated central shaft member having a small first diameter first end portion, a larger second diameter central portion, a second plurality of second end adjacent flat planar portions and a smaller third diameter second end portion all disposed in axial sequence therealong, said central shaft being telescopically receivable within said sleeve member with said second diameter shaft portion and said hollow interior sleeve portion in axially slidable close comformity and with said first diameter end portion and an exposed portion of said second diameter central portion extending axially beyond said sleeve slots;

a trephine cutter bit assembly receivable on said central shaft second end flat planar and third diameter end portions and within said sleeve member hollow portion at said second axially extending tab end thereof, said cutter bit assembly including a second plurality of sharpened tooth serrated end cutter bit segments each extending under said cylindrical sleeve member and disposed in a closed circular array around said shaft member third diameter end portion within said sleeve member tab end portion, each said segment having a flat interior surface engageable with one of said central shaft member flat planar portions at said sleeve member enclosed segment end and an exterior socket portion engageable with one of said axially extending elongated sleeve member tabs adjacent the exposed serrations end of said cutter bit segment; and a prime mover connected adjustable chuck having a hollow driving shaft and a first plurality of position movable jaw members, each receivable through one of said sleeve member slots in surrounding and gripping relationship on said elongated central shaft member exposed portion with said central shaft member first diameter first end portion received in said hollow driving shaft;

whereby torque from said chuck is transmitted to said cutter bit assembly sharpened teeth via both a first path through said central shaft member and said central shaft member and cutter bit engaged flat portions and by a second path through said chuck jaw engaged sleeve member slots, the body of said sleeve member and engagement between sleeve member tabs and cutter bit assembly socket portions, with the gripping of said central shaft member by said chuck jaws also holding said sleeve member and central shaft member in a predetermined fixed relative axial position operating relationship wherein said cutter bit assembly socket portions and sleeve member tabs are rigidly engaged, and said chuck jaws and sleeve member slots are rigidly engaged and said central shaft member and cutter bit segments are rigidly and surroundably engaged within said sleeve member.

14. The apparatus of claim 13 wherein said first plurality is three in number, there being three sleeve slots and three chuck jaw members in said apparatus.

15. The apparatus of claim 14 wherein said second plurality is two in number, there being two sleeve tabs, two cutter bit segments and two central shaft flat portions in said apparatus.

* * * * *

UNITED STATES PATENT AND TRADEMARK OFFICE
CERTIFICATE OF CORRECTION

PATENT NO. : 4,913,143
DATED : April 3, 1990
INVENTOR(S) : Clarence M. Oloff et al It is certified that error appears in the above-identified patent and that said Letters Patent is hereby corrected as shown below:

Col 3, line 38, "ship as" should be ---ship-as---.

Col 7, lines 9-14, delete the heading, "IN THE DRAWINGS", and the first two sentences of the paragraph starting with "Please substitute the enclosed..." and start the paragraph with "The trephine cutter unit is of ...".

Signed and Sealed this

Seventeenth Day of December, 1991

Attest:

HARRY F. MANBECK, JR.

*Attesting Officer*     *Commissioner of Patents and Trademarks*